US008774488B2

(12) United States Patent
Parikh et al.

(10) Patent No.: US 8,774,488 B2
(45) Date of Patent: Jul. 8, 2014

(54) METHOD AND DEVICE FOR IDENTIFICATION OF NUCLEATED RED BLOOD CELLS FROM A MATERNAL BLOOD SAMPLE

(75) Inventors: Bhairavi Parikh, Palo Alto, CA (US); Michael D. Brody, Fremont, CA (US); James Stone, Saratoga, CA (US); Jonathan D. Halderman, Santa Clara, CA (US)

(73) Assignee: Cellscape Corporation, Newark, CA (US)

( * ) Notice: Subject to any disclaimer, the term of this patent is extended or adjusted under 35 U.S.C. 154(b) by 0 days.

(21) Appl. No.: 13/046,543

(22) Filed: Mar. 11, 2011

(65) Prior Publication Data

US 2011/0311960 A1 Dec. 22, 2011

Related U.S. Application Data

(60) Provisional application No. 61/313,098, filed on Mar. 11, 2010.

(51) Int. Cl.
*G06K 9/00* (2006.01)
*A61K 39/395* (2006.01)
*C12N 5/071* (2010.01)

(52) U.S. Cl.
USPC ........... 382/134; 382/129; 382/130; 382/133; 424/130.1; 435/372; 435/968

(58) Field of Classification Search
USPC ............... 382/129, 130, 133, 134; 424/130.1; 435/372, 968
See application file for complete search history.

(56) References Cited

U.S. PATENT DOCUMENTS

| | | |
|---|---|---|
| 4,127,113 A | 11/1978 | Nollan |
| 4,223,257 A | 9/1980 | Miller |
| 4,544,629 A | 10/1985 | Rice et al. |
| 4,594,318 A | 6/1986 | Gusella et al. |
| 4,923,620 A | 5/1990 | Pall |
| 4,925,572 A | 5/1990 | Pall |
| 4,986,274 A | 1/1991 | Stephens |
| 5,001,050 A | 3/1991 | Blanco et al. |
| 5,081,030 A | 1/1992 | Civin |
| 5,239,170 A | 8/1993 | Hughlett |
| 5,275,933 A | 1/1994 | Teng et al. |
| 5,333,675 A | 8/1994 | Mullis et al. |
| 5,432,054 A | 7/1995 | Saunders et al. |
| 5,437,987 A | 8/1995 | Teng et al. |
| 5,447,842 A | 9/1995 | Simons |
| 5,457,024 A | 10/1995 | Goldbard |
| 5,459,073 A | 10/1995 | Ryan |
| 5,460,797 A | 10/1995 | Ryan |
| 5,489,386 A | 2/1996 | Saunders |
| 5,501,952 A | 3/1996 | Cubbage et al. |
| 5,521,061 A | 5/1996 | Bresser et al. |
| 5,541,072 A | 7/1996 | Wang et al. |
| 5,547,835 A | 8/1996 | Koster |
| 5,557,456 A | 9/1996 | Garner et al. |
| 5,582,982 A | 12/1996 | Cubbage et al. |
| 5,605,798 A | 2/1997 | Koster |
| 5,622,824 A | 4/1997 | Koster |
| 5,629,147 A | 5/1997 | Asgari et al. |
| 5,639,669 A | 6/1997 | Ledley |
| 5,641,628 A | 6/1997 | Bianchi |
| 5,646,001 A | 7/1997 | Terstappen et al. |
| 5,646,004 A | 7/1997 | Van Vlasselaer |
| 5,650,332 A | 7/1997 | Gao et al. |
| 5,662,813 A | 9/1997 | Sammons et al. |
| 5,663,051 A | 9/1997 | Vlasselaer |
| 5,665,546 A | 9/1997 | Cubbage et al. |
| 5,665,549 A | 9/1997 | Pinkel et al. |
| 5,668,117 A | 9/1997 | Shapiro |
| 5,676,849 A | 10/1997 | Sammons et al. |
| 5,707,801 A | 1/1998 | Bresser et al. |
| 5,714,325 A | 2/1998 | Bianchi |
| 5,716,776 A | 2/1998 | Bogart |
| 5,731,156 A | 3/1998 | Golbus |
| 5,750,339 A | 5/1998 | Smith |
| 5,759,766 A | 6/1998 | Nelson |
| 5,764,792 A | 6/1998 | Kennealy |
| 5,777,324 A | 7/1998 | Hillenkamp |
| 5,784,193 A | 7/1998 | Ferguson |

(Continued)

FOREIGN PATENT DOCUMENTS

| | | |
|---|---|---|
| JP | 2003279453 | 10/2003 |
| WO | WO 96/01438 A1 | 1/1996 |
| WO | WO 00/62247 A1 | 10/2000 |
| WO | WO 00/75709 A1 | 12/2000 |
| WO | WO2004/083369 | 9/2004 |
| WO | WO 2006/018849 A2 | 2/2006 |
| WO | WO 2010/078872 A2 | 7/2010 |
| WO | WO2011/140555 A2 | 11/2011 |

OTHER PUBLICATIONS

Angulo et al.; Automated detection of working area of peripheral blood smears using mathematical morphology; Analytical Cellular Pathology; 25(1); pp. 37R49; Jan. 2003.
Beckman Coulter; The Coulter LH 780 Hematology Systems (prod. Info.); 4 pgs.; 2009(accessed Mar. 15, 2012) (http://wayback.archive.org/web/*/http://www.beckmancoulter.com/literature/ClinDiag/BR-13034A.pdf).
Sysmex; Slide Preparation with Sysmex SP-Series; http://www.sysmex-europe.com/files/articles/Xtra_SP1000i.pdf; Sysmex Xtra Online, vol. 1, Jan. 2007.
Trommler et al.; Red Blood Cells Experience Electrostatic Repulsion but make Molecular Adhesions with Glass; Biophysical Journal; vol. 48; pp. 835-841; Nov. 1985.

(Continued)

*Primary Examiner* — Shin-Lin Chen
(74) *Attorney, Agent, or Firm* — Shay Glenn LLP

(57) ABSTRACT

A method for concentrating and isolating nucleated cells, such as a maternal and fetal nucleated red blood cells (NR-BC's), in a maternal whole blood sample. The invention also provides methods and apparatus for preparing to analyze and analyzing the sample for identification of fetal genetic material as part of prenatal genetic testing. The invention also pertains to methods and apparatus for discriminating fetal nucleated red blood cells from maternal nucleated red blood cells obtained from a blood sample taken from a pregnant woman.

30 Claims, 5 Drawing Sheets

(56) References Cited

U.S. PATENT DOCUMENTS

| | | |
|---|---|---|
| 5,789,414 A | 8/1998 | Lapidot et al. |
| 5,790,710 A | 8/1998 | Price et al. |
| 5,830,645 A | 11/1998 | Pinkel et al. |
| 5,834,203 A | 11/1998 | Katzir et al. |
| 5,840,502 A | 11/1998 | Van Vlasselaer |
| 5,843,644 A | 12/1998 | Liotta et al. |
| 5,854,033 A | 12/1998 | Lizardi |
| 5,854,075 A | 12/1998 | Levine et al. |
| 5,858,192 A | 1/1999 | Becker et al. |
| 5,861,488 A | 1/1999 | LeBoulch et al. |
| 5,888,370 A | 3/1999 | Becker et al. |
| 5,888,740 A | 3/1999 | Han |
| 5,900,481 A | 5/1999 | Lough et al. |
| 5,920,871 A | 7/1999 | Macri et al. |
| 5,928,906 A | 7/1999 | Koster et al. |
| 5,962,234 A | 10/1999 | Golbus |
| 5,985,153 A | 11/1999 | Dolan et al. |
| 5,993,630 A | 11/1999 | Becker et al. |
| 5,993,665 A | 11/1999 | Terstappen et al. |
| 6,013,188 A | 1/2000 | Terstappen et al. |
| 6,017,949 A | 1/2000 | D'Amato et al. |
| 6,020,137 A | 2/2000 | Lapidus et al. |
| 6,022,688 A | 2/2000 | Jurinke et al. |
| 6,024,925 A | 2/2000 | Little et al. |
| 6,027,889 A | 2/2000 | Barany et al. |
| 6,042,874 A | 3/2000 | Visinoni et al. |
| 6,043,031 A | 3/2000 | Koster et al. |
| 6,074,823 A | 6/2000 | Koster |
| 6,087,134 A | 7/2000 | Saunders |
| 6,090,625 A | 7/2000 | Abuljadayel |
| 6,096,876 A | 8/2000 | St. Arnaud et al. |
| 6,100,029 A | 8/2000 | Lapidus et al. |
| 6,100,033 A | 8/2000 | Smith et al. |
| 6,110,127 A | 8/2000 | Suzuki |
| 6,111,251 A | 8/2000 | Hillenkamp |
| 6,124,120 A | 9/2000 | Lizardi |
| 6,133,436 A | 10/2000 | Koster et al. |
| 6,136,182 A | 10/2000 | Dolan et al. |
| 6,136,540 A | 10/2000 | Tsipouras et al. |
| 6,140,053 A | 10/2000 | Koster |
| 6,143,495 A | 11/2000 | Lizardi et al. |
| 6,146,593 A | 11/2000 | Pinkel et al. |
| 6,146,854 A | 11/2000 | Koster et al. |
| 6,159,685 A | 12/2000 | Pinkel et al. |
| 6,169,816 B1 | 1/2001 | Ravkin |
| 6,184,973 B1 | 2/2001 | Baer et al. |
| 6,194,144 B1 | 2/2001 | Koster |
| 6,197,506 B1 | 3/2001 | Fodor et al. |
| 6,197,563 B1 | 3/2001 | Erlich et al. |
| 6,207,370 B1 | 3/2001 | Little et al. |
| 6,210,889 B1 | 4/2001 | Drouin et al. |
| 6,221,596 B1 | 4/2001 | Yemini et al. |
| 6,221,607 B1 | 4/2001 | Tsipouras et al. |
| 6,225,061 B1 | 5/2001 | Becker et al. |
| 6,251,615 B1 | 6/2001 | Oberhardt |
| 6,258,540 B1 | 7/2001 | Lo et al. |
| 6,268,131 B1 | 7/2001 | Kang et al. |
| 6,270,971 B1 | 8/2001 | Ferguson-Smith et al. |
| 6,309,822 B1 | 10/2001 | Fodor et al. |
| 6,320,174 B1 | 11/2001 | Tafas et al. |
| 6,323,009 B1 | 11/2001 | Lasken et al. |
| 6,331,395 B1 | 12/2001 | Burchell et al. |
| 6,406,843 B1 | 6/2002 | Skeeles et al. |
| 6,406,847 B1 | 6/2002 | Cox et al. |
| 6,418,236 B1 | 7/2002 | Ellis et al. |
| 6,432,630 B1 | 8/2002 | Blankenstein |
| 6,440,667 B1 | 8/2002 | Fodor et al. |
| 6,465,182 B1 | 10/2002 | Gray et al. |
| 6,472,215 B1 | 10/2002 | Huo et al. |
| 6,500,938 B1 | 12/2002 | Au-Young et al. |
| 6,524,798 B1 | 2/2003 | Goldbard et al. |
| 6,544,751 B1 | 4/2003 | Brandwein et al. |
| 6,548,259 B2 | 4/2003 | Ward et al. |
| 6,551,784 B2 | 4/2003 | Fodor et al. |
| 6,569,621 B1 | 5/2003 | Cremer et al. |
| 6,596,143 B1 | 7/2003 | Wang et al. |
| 6,617,158 B1 | 9/2003 | Bohmer |
| 6,641,708 B1 | 11/2003 | Becker et al. |
| 6,642,365 B1 | 11/2003 | Lapidot et al. |
| 6,645,388 B2 | 11/2003 | Sheikh-Ali et al. |
| 6,673,541 B1 | 1/2004 | Klein et al. |
| 6,716,642 B1 | 4/2004 | Wu et al. |
| 6,744,038 B2 | 6/2004 | Wang et al. |
| 6,759,663 B2 | 7/2004 | Tsipouras et al. |
| 6,784,420 B2 | 8/2004 | Wang et al. |
| 6,790,636 B1 | 9/2004 | Star et al. |
| 6,803,195 B1 | 10/2004 | Avivi et al. |
| 6,815,664 B2 | 11/2004 | Wang et al. |
| 6,833,542 B2 | 12/2004 | Wang et al. |
| 6,852,534 B2 | 2/2005 | Wernet et al. |
| 6,858,439 B1 | 2/2005 | Xu et al. |
| 6,881,314 B1 | 4/2005 | Wang et al. |
| 6,905,823 B2 | 6/2005 | Kallioniemi et al. |
| 6,911,315 B2 | 6/2005 | Rimm et al. |
| 6,916,658 B2 | 7/2005 | Li et al. |
| 6,926,915 B2 | 8/2005 | Yura et al. |
| 6,927,028 B2 | 8/2005 | Dennis et al. |
| 6,949,355 B2 | 9/2005 | Yamanishi et al. |
| 6,956,695 B2 | 10/2005 | Tafas et al. |
| 6,977,162 B2 | 12/2005 | Dhallan |
| 6,993,187 B2 | 1/2006 | Recht |
| 7,015,047 B2 | 3/2006 | Huang et al. |
| 7,062,079 B2 | 6/2006 | Recht |
| 7,081,192 B1 | 7/2006 | Wang et al. |
| 7,094,292 B2 | 8/2006 | Randall et al. |
| 7,113,624 B2 | 9/2006 | Curry |
| 7,153,648 B2 | 12/2006 | Jing et al. |
| 7,153,652 B2 | 12/2006 | Cox et al. |
| 7,160,992 B2 | 1/2007 | Lapidot et al. |
| 7,166,443 B2 | 1/2007 | Walker et al. |
| 7,196,788 B2 | 3/2007 | Tsipouras et al. |
| 7,208,274 B2 | 4/2007 | Dhallan et al. |
| 7,214,427 B2 | 5/2007 | Huang et al. |
| 7,220,412 B2 | 5/2007 | Abuljadayel |
| 7,238,484 B2 | 7/2007 | Pinkel et al. |
| 7,262,016 B2 | 8/2007 | Huang et al. |
| 7,277,569 B2 | 10/2007 | Bruce et al. |
| 7,279,277 B2 | 10/2007 | Hulten |
| 7,280,261 B2 | 10/2007 | Curry et al. |
| 7,286,224 B2 | 10/2007 | Curry et al. |
| 7,300,804 B2 | 11/2007 | Sellek-Prince |
| 7,332,277 B2 | 2/2008 | Dhallan |
| 7,335,470 B2 | 2/2008 | Mohammed et al. |
| 7,346,200 B1 | 3/2008 | Tsipouras et al. |
| 7,351,529 B2 | 4/2008 | Mohammed |
| 7,354,733 B2 | 4/2008 | Bukshpan et al. |
| 7,364,921 B1 | 4/2008 | Sciorra et al. |
| 7,410,773 B2 | 8/2008 | Abuljadayel |
| 7,437,249 B2 | 10/2008 | Corson et al. |
| 7,439,062 B2 | 10/2008 | Bhatt et al. |
| 7,439,346 B2 | 10/2008 | Johnson et al. |
| 7,442,506 B2 | 10/2008 | Dhallan |
| 7,468,249 B2 | 12/2008 | Xie et al. |
| 7,507,539 B2 | 3/2009 | Owen et al. |
| 7,534,567 B2 | 5/2009 | Albertson et al. |
| 7,537,938 B2 | 5/2009 | Kirakossian et al. |
| 7,563,586 B2 | 7/2009 | Okuse et al. |
| 7,589,309 B2 | 9/2009 | Tafas |
| 7,640,112 B2 | 12/2009 | Tsipouras et al. |
| 7,645,576 B2 | 1/2010 | Lo et al. |
| 7,651,838 B2 | 1/2010 | Paterlini-Brechot |
| 7,660,454 B2 | 2/2010 | Kilpatrick et al. |
| 7,660,675 B2 | 2/2010 | Ghosh et al. |
| 7,702,468 B2 | 4/2010 | Chinitz et al. |
| 7,718,419 B2 | 5/2010 | Wu et al. |
| 7,723,029 B2 | 5/2010 | Huang et al. |
| 7,727,720 B2 | 6/2010 | Dhallan |
| 7,745,221 B2 | 6/2010 | Butler et al. |
| 7,785,898 B2 | 8/2010 | Bohmer |
| 7,799,531 B2 | 9/2010 | Mitchell et al. |
| 7,881,876 B2 | 2/2011 | Le Cocq et al. |
| 7,888,017 B2 | 2/2011 | Quake et al. |
| 7,892,743 B2 | 2/2011 | Owen et al. |
| 8,021,614 B2 | 9/2011 | Huang et al. |

(56) References Cited

U.S. PATENT DOCUMENTS

| | | | |
|---|---|---|---|
| 8,027,823 | B2 | 9/2011 | Barrett et al. |
| 8,168,389 | B2 | 5/2012 | Shoemaker et al. |
| 2001/0008461 | A1* | 7/2001 | Koyama et al. ............... 359/380 |
| 2002/0045196 | A1 | 4/2002 | Mahoney et al. |
| 2002/0081014 | A1 | 6/2002 | Ravkin |
| 2002/0090623 | A1 | 7/2002 | Smith et al. |
| 2002/0187202 | A1* | 12/2002 | Goswami et al. ............. 424/559 |
| 2003/0036100 | A1 | 2/2003 | Fisk et al. |
| 2003/0165852 | A1 | 9/2003 | Schueler et al. |
| 2003/0180762 | A1 | 9/2003 | Tuma et al. |
| 2003/0232377 | A1 | 12/2003 | Thomas |
| 2004/0029103 | A1 | 2/2004 | Robinson et al. |
| 2004/0091880 | A1 | 5/2004 | Wiebusch et al. |
| 2004/0170765 | A1 | 9/2004 | Ederer et al. |
| 2005/0164241 | A1 | 7/2005 | Hahn et al. |
| 2005/0208501 | A1 | 9/2005 | Goldrick |
| 2005/0214758 | A1* | 9/2005 | Yura et al. |
| 2006/0040305 | A1 | 2/2006 | Fejgin et al. |
| 2006/0105353 | A1 | 5/2006 | Jalal et al. |
| 2006/0134599 | A1 | 6/2006 | Toner et al. |
| 2007/0072167 | A1 | 3/2007 | Rochaix |
| 2007/0105105 | A1 | 5/2007 | Clelland et al. |
| 2007/0202536 | A1* | 8/2007 | Yamanishi et al. |
| 2007/0211460 | A1 | 9/2007 | Ravkin |
| 2007/0218558 | A1 | 9/2007 | Ortiz et al. |
| 2008/0026390 | A1 | 1/2008 | Stoughton et al. |
| 2008/0050739 | A1 | 2/2008 | Stoughton et al. |
| 2008/0057505 | A1 | 3/2008 | Lin et al. |
| 2008/0113358 | A1 | 5/2008 | Kapur et al. |
| 2008/0138809 | A1 | 6/2008 | Kapur et al. |
| 2008/0241848 | A1 | 10/2008 | Tsipouras et al. |
| 2008/0318235 | A1 | 12/2008 | Handyside |
| 2009/0111101 | A1 | 4/2009 | Tafas et al. |
| 2009/0220933 | A1 | 9/2009 | Kolvraa et al. |
| 2009/0220955 | A1* | 9/2009 | Verrant |
| 2009/0253145 | A1 | 10/2009 | Kilpatrick et al. |
| 2010/0035246 | A1 | 2/2010 | Lushi et al. |
| 2010/0159506 | A1 | 6/2010 | Parikh et al. |
| 2010/0184069 | A1 | 7/2010 | Fernando et al. |
| 2010/0304978 | A1 | 12/2010 | Deng et al. |
| 2011/0027771 | A1 | 2/2011 | Deng |
| 2011/0178719 | A1* | 7/2011 | Rabinowitz et al. |
| 2011/0230362 | A1 | 9/2011 | Craig et al. |
| 2012/0053062 | A1 | 3/2012 | Brooks |
| 2013/0096011 | A1 | 4/2013 | Rava et al. |
| 2013/0137137 | A1 | 5/2013 | Brody et al. |
| 2013/0345084 | A1 | 12/2013 | Stone |

OTHER PUBLICATIONS

Wachi et al.; Studies on preliminary concentration methods for recovery of fetal nucleated red blood cells in maternal blood; Congenital Anomalies (Kyoto); 44(4): 196-203; Dec. 2004.

Wolf et al.; Conformational Response of the Glycocalyx to Ionic Strength and Interaction with Modified Glass Surfaces: Study of Live Red Cells by Interferometry; Journal of Cell Science; vol. 63; pp. 101-112; Sep. 1983.

Xia et al.; Kinetics of Specific and Nonspecific Adhesion of Red Blood Cells on Glass; Biophysical Journal; vol. 65; pp. 1073-1083; Sep. 1993.

Xiong et al.; Automatic Working Area Classification in Peripheral Blood Smears Using Spatial Distribution Features Across Scales; 19th Int. Conf. on Pattern Recognition, ICPR 2008; pp. 1-4; Dec. 2008.

Zhao et al.; An immunoassay to detect human embryonic globin chains by a murine monoclonal antibody; Blood; 71(4); pp. 883-887; Apr. 1988.

ACOG Practice Bulletin Clinical Management Guidelines for Obstetrician-Gynecologists,No. 77, Jan. 2, 2007: "Screening for Fetal Chromosomal Abnormalities" Obstetrics & Gynecology, Jan. 2007; 109(1): 217-227. <<http://ljournals.lww.com/greenjournai/Citation/2007/01000/ACOG_Practice_Bulletin_No_77_Screening_for_Fetal.54.aspx>>.

American College of OB/GYN(s); Routine tests during pregnancy; Medem Med. Library; 2000 (medem.com/MedLB/article_detaillb.cfm?article_ID=ZZZ84JKXODCC_cat=2005); printed Oct. 12, 2011.

American Pregnancy Association, "Prenatal Testing" <<http://american preg nancy.org/prenataltesting/>>, printed Oct. 20, 2009.

Bajaj et al., "Ultra-rare-event detection performance of a custom scanning cytometer on amodel preparation of fetal nRBCs," Cytometry Part A. 2000; 39(4):2852-94.

Cha et al., "A simple and sensitive erythroblast scoring system to identify fetal cells in maternal blood," Prenat Diagn 2003; 23(1):68-73.

Chong et al.; Recovery of Human Leukocytes from a Leukocyte-Depletion Filter; J. Transfusion; vol. 32; No. 85; Oct. 1992 (Abstract).

Choolani et al., "Characterization of first trimester fetal erythroblasts for non-invasive prenatal diagnosis," Molecular Human Reproduction. Apr. 2003; 9(4):227-235. Retrievedfrom the Internet: <21 http:/lmolehr.oxfordjournals.org/cgi/reprint/9/4/227>>.

Choolani et al., "Simultaneous fetal cell identification and diagnosis by epsilon-globin chain immunophenotyping and chromosomal fluorescence in situ hybridization," Blood.2001; 98:554-557. Retrieved from the Internet:<<http://bloodjournal.hematologylibrary.org/cgi/reprint/98/3/554.pdf>>.

Davies et al.; Cell crushing: a technique for greatlyreducing errors in microspectrometry; Exp Cell Res; vol. 6; No. 2; pp. 550-553; 1954.

Ebner et al.; Generation of large numbers of human dendritic cells from whole blood passaged through leukocyte removal filters: an alternative to standard buffy coats; J. Immunological Methods; vol. 252; pp. 93-104; 2001.

Goh et al.; The human reticulocyte transcriptome; Physiol Genomics; vol. 30; pp. 172-178; 2007.

Ho et al., "Fetal cells in maternal blood: State of the art for non-invasive prenatal diagnosis," Ann Acad Med Singapore. Sep. 2003; 32(5):597-604. Retrieved from the Internet:<<http://www.annals.edu.sg/pdfSep03/V32N5p597.pdf>>.

Joutovsky et al.; HPLC retention time as a diagnostic toll for hemoglobin variants and hemoglobinopathies: a study of 60 000 samples in a clinical diagnostic laboratory; Clinical Chemistry. 2004.50: 1736-1747.

Kwon et al., "A high yield of fetal nucleated red blood cells isolated using optimal osmolalityand a double-density gradient system," Prenat Diagn. 2007; 27(13):1245-1250.

Longley et al.; Recovery of functional human lymphocytes from Leukotrapfilters; J Immunol Methods; 121(1); pp. 33-38; Jul. 1989.

Maruyama et al.; Simultanious direct counting of total and specific microbial cells in seawater, using a deep-sea microbe as target; Applied Enviro Micro. 2000. 66: 2211-2215.

Mavrou et al., "Identification of nucleated red blood cells in maternal circulation: A second step in screening for fetal aneuploidies and pregnancy complications," Prenat Diagn. Feb. 2007; 27:150-153.

Mavrou et al.; Improved specificity of NRBC detection in chorionic villus sample supernatant fluids using anti-zetaand anti-epsilon monoclonal antibodies; Fetal Diagn Ther; vol. 14; No. 5; pp. 291-295; Sep. 1999.

May-Grünwald-Giemsa Staining Description, posted on<<http//:cellbio.dote.hu/angol/description_maygrunwald.pdf>> on Dec. 10, 2008.

Merchant et al., "Strategies for automated fetal cell screening," Human Reproduction Update 2002; 8 (6):509-521. Retrieved from the Internet: <<http:/lhumupd.oxfordjournals.org/cgi/reprint/8/6/509>>.

Meyer Instruments, Imaging Software—Surveyor Software with Turboscan. Retrieved from the Internet: <<http://www.meyerinst.com/html/objectiveimaging/default.htm>>, lastmodified Jan. 17, 2006.

Mickols et al.; Visualization of oriented hemoglobin S in individual erythrocytes by differential extinction of polarized light; PNAS. 1985.82:6527-6531.

Migeon et al.; Species differences in TSIX/Tsix reveal the roles of these genes in X-chromosome inactivation; Am J Hum Genet; vol. 71; pp. 286-293; 2002.

(56) References Cited

OTHER PUBLICATIONS

Mohandas et al.; Adhesion of Red Cells to Foreign Surfaces in the Presence of Flow; Journal of Biomedical Material Research; vol. 8; pp. 119-136; 1974.
Neu et al.; Depletion Interactions in Polymer Solutions Promote Red Blood Cell Adhesion to Albumin-coated Surfaces; Biochim Biophys Acta.; vol. 1760; No. 12; pp. 1772-1779; 2006.
Olney et al.; Chorionic villus sampling and amniocentesis: recommendations for prenatal counseling; MMWR; 44 (RR-9); pp. 1-12; Jul. 21, 1995 (wonder.cdc.gov/wonder/prevguid/m0038393/m0038393.asp); printed Oct. 12, 2011.
Oosterwijk et al., "Strategies for rare-event detection: an approach for automated fetalcelldetection in maternal blood," Am J Hum Genet.1998; 63(2):1783-1792.
Oplenic "DAF1000 Microscope Digital Auto focus system" [Product Description], 2 pages total. Retrieved from the Internet:<<http://www.bikudo.com/product_search/details/67615/daf1000_microscope_digital_auto_focus system.html#desc>> printed Oct. 20, 2009.
Pietersz et al.; Comparison of five different filters for the removal of leukocytes from red cell concentrates; Vox Sang; 1992 ; 62(2); pp. 76-81.
Purwosunu et al.; Clinical potential for noninvasive prenatal diagnosis through detection of fetal cells in maternal blood; Taiwanese J Obstet Gynecol; vol. 45; No. 1; pp. 10-20; Mar. 2006.
Purwosunu et al.; Enrichment of NRBC in maternal blood: a more feasible method for noninvasive prenatal diagnosis; Prenat Diagn; vol. 26; No. 6; pp. 545-547; Jun. 2006.
QC Sciences, NuFix} Complete Collection Solution [Product Description], 1 page, 2008.
Ravkin et al. Proceedings of SPIE (Optical Investigation of Cells In Vitro and In Vivo), v. 3260, pp. 180-191, 1998.
Singh-Zocchi et al.; Osmotic Pressure Contribution of Albumin to Colloidal Interactions; Proc. of the Nat. Academy of Sciences, USA; 96: pp. 6711-6715; 1999.
Tachev et al.; Erythrocyte Attachment to Substrates: Determination of Membrane Tension and Adhesion Energy; Colloids and Surfaces B: Biointerfaces; vol. 19: 61-80; 1999.
Troeger et al., "Approximately half of the erythroblasts in maternal blood are of fetal origin," Molecular Human Reproduction, 1999; 5(12):1162-1165. Retrieved from the Internet:<<http:lmolehr.oxfordjournals.org/cgi/reprint/5/12/1162>>.
Vogler; A Thermodynamic Model of Short-Term Cell Adhesion in Vitro; Colloids and Surfaces; vol. 42; pp. 233-254; 1989.
Wachtel et al.; Fetal cells in maternal blood; Clinical Genetics; vol. 59; pp. 74-79; 2001.
Wagner, Lana, "Diagnosis and management of preeclampsia," Am Fam Physician. Dec. 2004;70:2317-2324. Retrieved from the Internet: <<http://www.aafp.org/afp/20041215/2317.pdf>>.
Wataganara et al., "Fetal cell-free nucleic acids in the maternal circulation: new clinicalapplications," Ann NY Acad Sci. 2004; 1022:90-99.
Weitkamp et al.; Blood donor leukocyte reduction filters as a source of human B lymphycytes; BioTechniques; vol. 31; pp. 464, 466; Sep. 2001.
Yamanishi et al.; Enrichment of rare fetal cells from maternal peripheral blood; ExpertRev Mol Diagn; 2(4); pp. 303-311; 2002 (Abstract Only).
Zheng et al.; Fetal cell identifiers: results of microscope slide-based immunocytochemicalstudies as a function of gestational age and abnormality; Am J Obstet Gynecol; vol. 180; No. 5; pp. 1234-1239; May 1999.
Parikh et al.; U.S. Appl. No. 13/247,896 entitled "Method and Device for Identification of Nucleated Red Blood Cells from a Maternal Blood Sample," filed Sep. 28, 2011.
Benattar et al.; Comparison of the classical manual pushed wedge films, with an improved automated method for making blood smears; Hematol Cell Ther; 41(5); pp. 211-215; Nov. 1999.
Xiong et al.; Automatic working area classification in peripheral blood smears without cell central zone extraction; 30th Annual Int. Conf Proc IEEE Eng Med Biol Soc; pp. 4074-4077; Aug. 2008.
George et al.; Adhesion of Human Erythrocytes to Glass: The Nature of the Interaction and the Effect of Serum and Plasma; J. Cell Physiology; 77(1); pp. 51-59; Feb. 1971.
George, James N.; Fibrinogen Inhibits Red Cell Adhesion to Glass; J. Cell Physiology; 79(3); pp. 457-461; Jun. 1972.
Jang et al.; Effects of Chemical Etching with Sulfuric Acid on Glass Surface; Journal of Vacuum Science Technology A 18(2); pp. 401-404; Mar. 2000.
Jang et al.; Effects of Chemical Etching with Nitric Acid on Glass Surface; Journal of Vacuum Science Technology A; 19(1); pp. 267-274; Jan./Feb. 2001.
Cras et al.; Comparison of Chemical Cleaning Methods of Glass in Preparation for Silanization; Biosensors and Bioelectronics; 14(8-9); pp. 683-688; Dec. 1999.
Parikh et al.; U.S. Appl. No. 13/681,251 entitled "Methods, Devices, and Kits for Obtaining and Analyzing Cells," filed Nov. 19, 2012.
Parikh et al.; U.S. Appl. No. 13/681,274 entitled "Methods and Devices for Obtaining and Analyzing Cells," filed Nov. 19, 2012.
Parikh et al.; U.S. Appl. No. 13/681,296 entitled "Methods and Devices for Obtaining and Analyzing Cells," filed Nov. 19, 2012.
Stone, James; U.S. Appl. No. 13/681,323 entitled "Methods and Devices for Obtaining and Analyzing Cells," filed Nov. 19, 2013.
Wikipedia, the free encyclopedia; File: Postnatal genetics en.svg; Feb. 4, 2011; downloaded from the internet: <http://en.wikipedia.org/wiki/File:Postnatal_genetics_en.svg> (printed Feb. 12, 2013).
Wood, W.G.; Haemoglobin Synthesis during Human Fetal Development; Br. Med. Bull.; 32(3):282-7; Sep. 1976.
Cha et al.; The utility of an erythroblast scoring system and gender-independent short tandem repeat (STR) analysis for the detection of aneuploid fetal cells in maternal blood; Prenat Diagn; 25; pp. 586-591; Jul. 2005.
Samura et al.; Diagnosis of trisomy 21 in fetal nucleated erythrocytes from maternal blood by use of short tandem repeat sequences; Clinical Chemistry; 47(9); pp. 1622-1626; Sep. 2001.
Sharma et al.; Leukocyte-Reduced Blood Transfusions: Perioperative Indications, Adverse Effects, and Cost Analysis; Anesth Analg; vol. 90; No. 6; pp. 1315-132; Jun. 2000.
DeMaria et al.; Improved Fetal Nucleated Erythrocyte Sorting Purity Using Intracellular Antifetal Hemoglobin and Hoechst 33342; Cytometry; 25(1):37-45; Sep. 1, 1996.
Dover et al.; Quantitation of Hemoglobins Within Individual Red Cells: Asynchronous Biosynthesis of Fetal and Adult Hemoglobin During Erythroid Maturation in Normal Subjects; Blood; 56(6):1082-1091; Dec. 1980.
Iyer et al.; Production of Murine Monoclonal Antibody to Fetal Hemoglobin; Hemoglobin; 27(4):229-234; Nov. 2003.
Sekizawa et al; Noninvasive Prenatal Diagnosis Using a Single Fetal Nucleated Erythrocyte Isolated by Micromanipulation from Maternal Blood; Methods Mol Med; 16:275-285; Mar. 2, 1998.
Zheng et al.; Prenatal diagnosis from maternal blood: simultaneous immunophenotyping and FISH of fetal nucleated erythrocytes isolated by negative magnetic cell sorting; J Med Genet; 30:1051-1056; Dec. 1993.
Kowalczynska et al; Albumin Adsorption On Unmodified And Sulfonated Polystyrene Surfaces, In Relation To Cell-Substratum Adhesion; Colloids and Surfaces B; Biointerfaces; 84(2); pp. 536-544; Jun. 2011.
Takabayashi et al; Development Of Non-Invasive Fetal DNA Diagnosis From Maternal Blood; Prenatal Diagnosis; 15(1); pp. 74-77; Jan. 1995.

\* cited by examiner

| | 1 | 2 | 3 | 4 | 5 | 6 | 7 | 8 |
|---|---|---|---|---|---|---|---|---|
| • 20 ml Start<br>• 150 ul Final<br>• >90% Scannable | | | | | | | | |
| RBC:WBC | 2.6:1 | 1.4:1 | 1.2:1 | 1.7:1 | 1.2:1 | 1.7:1 | 1.5:1 | 1.1:1 |
| Total Area to Scan (cm$^2$) | 302 | 324 | 324 | 324 | 205 | 302 | 400 | 324 |
| % Packing Density | 43% | 53% | 70% | 40% | 70% | 50% | 30% | 50% |
| % of Sample Analyzed | 3/28 | 3/30 | 4/30 | 6/30 | 1/19 | 4/28 | 1/37 | |
| #fnRBC's Identified | 8 | 3 | 4 | 4 | 4 | 4 | 3 | |
| #fnRBC's Extrapolated | 73 | 30 | 30 | 25 | 76 | 28 | 111 | |

FIG. 6

METHOD AND DEVICE FOR IDENTIFICATION OF NUCLEATED RED BLOOD CELLS FROM A MATERNAL BLOOD SAMPLE

CROSS REFERENCE TO RELATED APPLICATIONS

This application claims the benefit under 35 U.S.C. §119 of U.S. Appl. No. 61/313,098, filed Mar. 11, 2010, the disclosure of which is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

Prenatal genetic testing requires access to fetal DNA. As described in commonly owned US Patent Appl. Publ. No. 2010/0159506, fetal genetic material can be found within fetal cells present in the mother's circulating blood. These fetal cells originate in the fetus and cross the placenta to enter the mother's circulatory system.

Maternal blood contains both nucleated (i.e., containing genetic material) and non-nucleated cells of both fetal and maternal origin. In order to focus attention on the cells of most interest, a first step in fetal genetic testing may therefore be to concentrate nucleated cells within the sample. One prior approach is described in US Patent Appl. Publ. No. 2010/0159506. Since red blood cells are denser than white blood cells, a preliminary separation of red blood cells is obtained by a single density gradient to separate mononuclear cells, including nucleated red blood cells, from a whole blood sample. The sample is then applied to a slide in a monolayer, stained, and analyzed.

SUMMARY OF THE INVENTION

The present invention provides a method for concentrating and isolating nucleated cells, such as maternal and fetal nucleated red blood cells (NRBC's), from a maternal whole blood sample. The invention also provides methods and apparatus for preparing to analyze and analyzing the sample for identification of fetal genetic material as part of prenatal genetic testing. The invention also pertains to methods and apparatus for discriminating fetal nucleated red blood cells from maternal nucleated red blood cells obtained from a blood sample taken from a pregnant woman.

One aspect of the invention provides a method of enriching for fetal nucleated cells (such as, e.g. nucleated red blood cells) from a maternal blood sample. In some embodiments, the method includes the following steps: passing a maternal blood sample containing maternal nucleated cells and fetal nucleated cells through a filter (such as, e.g., a leukocyte depletion filter); retaining nucleated cells on the filter; and eluting nucleated cells from the filter with an elution buffer wherein the nucleated cells include fetal nucleated cells.

In some embodiments, the method also includes the step of staining the blood sample, such as by staining the blood sample with a nuclear stain.

In some embodiments, the method also includes the step of concentrating and resuspending the blood sample before the passing step, such as by centrifugation.

In some embodiments, the method also includes the step of measuring the blood sample before concentrating to, e.g., standardize an amount of cells in the blood sample.

Another aspect of the invention provides a method of creating a layer of cells on a surface including the following steps: moving a sample of cells in at least two directions relative to a surface to create a monolayer of cells on the surface; and adhering the cells to the surface. The movement may include, e.g., circular movement, zigzag movement, diagonal movement and/or serpentine movement. The relative movement may also include moving a portion of the sample away from the surface.

Some embodiments employ a smear tool in the moving step. In some such embodiments, the angle of the tool with respect to the surface may be varied. The relative speed of the tool with respect to the surface may also be varied, for example, in the range of 0.1 mm/sec to 500 mm/sec.

The moving step may include the step of generating a generally uniform sample density. Some embodiments also include the step of monitoring the density of the sample relative to the surface, such as by using red or blue light.

Yet another aspect of the invention provides a method of identifying a nucleated fetal cell. In some embodiments the method includes the steps of: adhering nucleated cells from a maternal blood sample to a surface, the surface comprising a plurality of portions; generating a pair of images corresponding to at least one portion of the surface; applying an algorithm to the pair and determining if the portion includes a cell of interest; and performing an analysis using a fetal identifier on at least one portion of the surface that includes a cell of interest and thereby determine if the at least one portion contains a fetal cell. In some embodiments, the analysis is selected from the group consisting of in situ hybridization and immunohistochemistry, and the method further includes the step of scanning the surface with an automated microscope after the adhering step. Some embodiments include the step of generating a third image.

In some embodiments, the step of generating a pair of images further includes the step of generating a first image with transmitted illumination and a second image with coaxial illumination. In various embodiments the wavelength of the transmitted illumination may be between 380 nm and 800 nm, above 620 nm, or around 420 nm. The coaxial illumination may be between 350 nm and 364 nm.

In some embodiments, the step of performing an analysis includes the step of selectively placing fetal identifiers on a plurality of portions of the surface, wherein each portion contains a candidate fetal cell.

In some embodiments, the step of applying an algorithm includes the steps of flattening at least one image; segmenting at least one image and thereby define foreground and background pixels; removing background pixels from at least one image to generate a transformed image; enumerating nuclei in the transformed image to generate enumerated nuclei; and calculating at least one of complexity and brightness for at least one enumerated nuclei, wherein low complexity or high brightness indicate a fetal cell character.

In some embodiments, the applying step further includes the steps of calculating a brightness of a background of the surface and a brightness of a foreground of a surface, and comparing a measurement of the pair of images to one or both of the background brightness and the foreground brightness.

Some embodiments include the additional step of storing a location of the pair of images. A nucleated cell may be located based on such a stored location.

Some embodiments include the step of fixing the sample with a non-cross linking fixative before the performing an analysis step and/or fixing the sample at a reduced temperature before the performing an analysis step.

In some embodiments, the performing step may include the step of treating with a stabilizer and/or treating with an antibody selected from the group consisting of anti zeta hemoglobin and anti epsilon hemoglobin if the analysis is immunohistochemistry.

Still another aspect of the invention provides a method of identifying a genetic status of a fetus. In some embodiments the method includes the following steps: adhering nucleated cells from a maternal blood sample to a surface, the surface comprising a plurality of portions; generating a pair of images corresponding to at least one portion; applying an algorithm to the pair of images and determining if the portion includes a cell of interest; performing an analysis using a fetal identifier on at least one portion of the surface that includes a cell of interest and thereby determine if the at least one portion contains a fetal cell (such as, e.g., by in situ hybridization and/or immunohistochemistry); and performing an analysis using a genetic identifier on at least one portion of the surface that includes a fetal cell and thereby determine the genetic status of the fetus (such as, e.g., by RNA in situ hybridization, DNA in situ hybridization and/or immunohistochemistry). The two performing steps may be performed at the same time.

Some embodiments may include the additional step of applying a pressure on the surface that is lower than atmospheric pressure during the performing step(s). The method may also include the step of crushing at least one cell of interest and an associated nuclei prior to the performing the analysis step.

Yet another aspect of the invention provides a method of identifying a fetal cell. In some embodiments, the method includes the following steps: providing a maternal blood sample; and performing in situ hybridization using a TSIX probe on the sample to generate a signal wherein a positive signal using a TSIX probe is indicative of the presence of fetal cellular material. The method may also include the step of separating the sample to generate a plurality of portions before the performing step to, e.g., provide a monolayer of cells.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 6 shows cell analysis results after enriching for fetal nucleated cells according to one aspect of the disclosure.

DETAILED DESCRIPTION OF THE INVENTION

Leukocyte depletion filters can be used to filter blood products from whole blood. Information about leukocyte depletion filters may be found in the following: U.S. Pat. No. 5,676,849; U.S. Pat. No. 5,662,813; U.S. Pat. No. 6,544,751; U.S. Pat. No. 4,923,620; U.S. Pat. No. 4,925,572; Comparison of Five Different Filters for Removal of Leukocytes from Red Cell Concentrates; VOX Sang 1992/62:76-81; Recovery of Human Leukocytes from a Leukodepletion Filter; Chang et al; J. Transfusion 1992/32 (85); Recovery of Functional Human Lymphocytes from Leukotrap Filters; Longley et al.; J. Immunological Methods; 1999/121:33-38; Biotechniques 31:464-466 (2001); S. Ebner et al.; J. Immunological Methods; 2001(252):93-104. In one aspect of the invention, such filters can be used to separate nucleated blood cells from non-nucleated blood cells.

According to one embodiment, a first step of the method is filtration. The incoming blood sample is filtered (e.g., within 24 hours of draw, preferably within 12 hours of draw) using a leukocyte depletion filter. A suitable leukocyte depletion filter is the PureCell™ Select System from Pall Corporation.

Custom chemistry may be used for cell suspension during the filtration process. The chemistry may include trehalose, maltose, dextran, pseudoephedrine, fluoride, phosphate and/or sulfate. The chemistry may address issues related to the degradation of cells during processing using the manufacturer's recommended process; improve the cell morphology in the final sample and may enable the unique DAPI+420 nm imaging process; reduce cell clumping and sphering which improves the ability to spread the cells evenly in a large area monolayer; stabilize the cells and provide more margin in terms of the time between the start of the filtration process and the creation of the monolayer; and reduce cell destruction and release of DNA into the suspension. The chemistry may also be used to increase the allowable time between blood draw and processing which will expand the population of candidate patients by opening the test to doctors in areas that are not near metropolitan centers.

Figure 1:
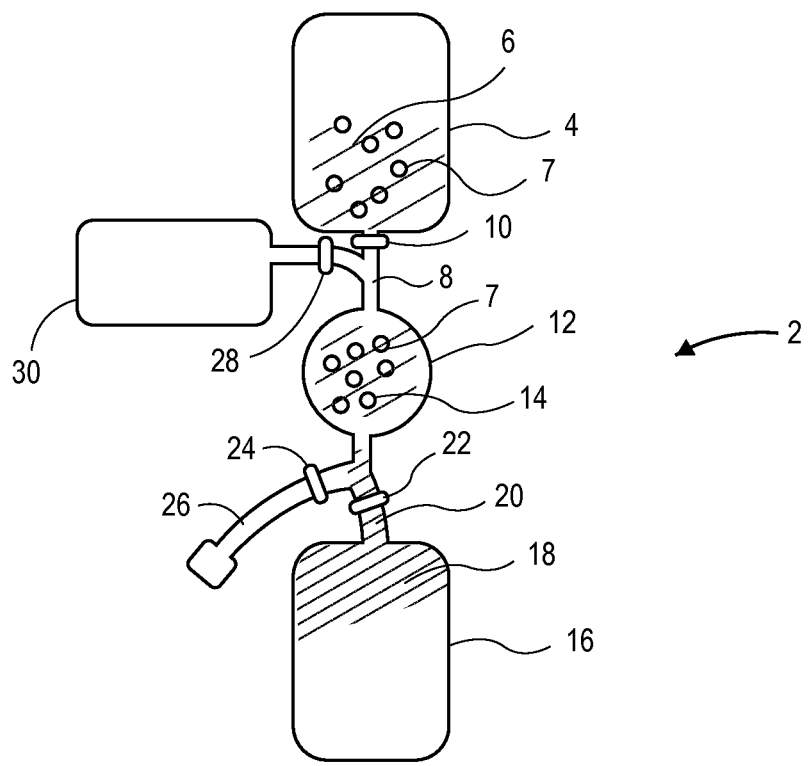
FIGS. 1-2 show a process and device for enriching for fetal nucleated cells from a blood sample using a filter system.
Figure 2:
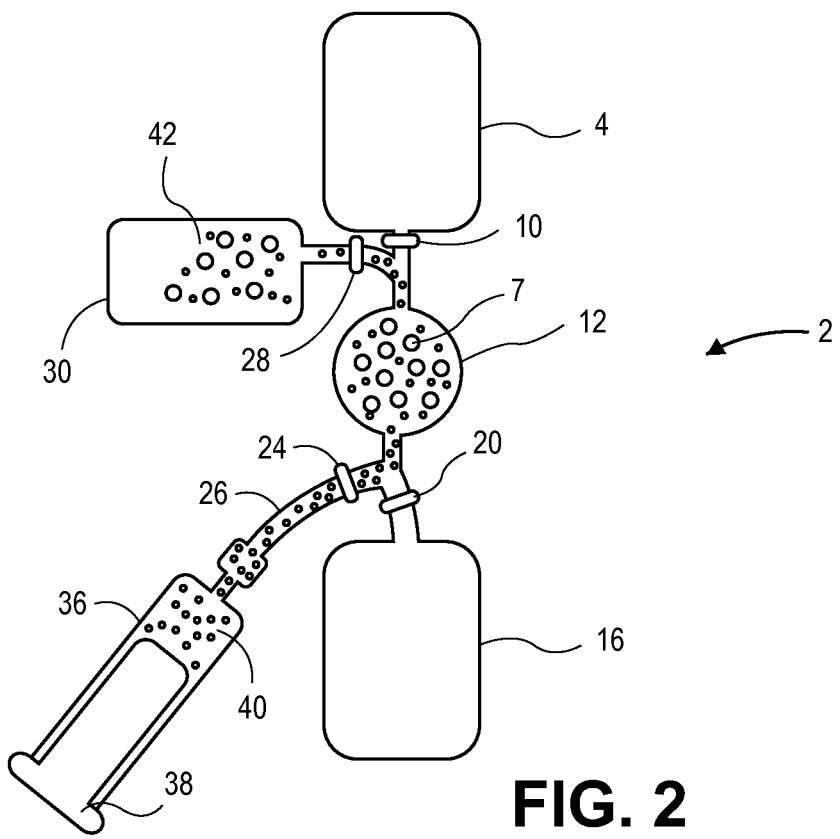

FIGS. 1-2 show a process and device for enriching for fetal nucleated cells from a blood sample using a filter system according to one embodiment of the invention. A maternal blood sample 6 containing various components of red blood including nucleated maternal and fetal nucleated cells 7 such as fetal nucleated red blood cells, is contained in bag 4. Valve 28 connecting tubing 8 to collection bag 30 and valve 24 connecting tubing 20 to tubing for elution 26 are closed. Valve 10 connecting tubing 8 to filter 12 is opened and blood sample 6 is passed through filter 12. Cells for collection 14, including nucleated fetal cells 7, remain behind on filter 12, while unwanted blood products 18, including mature reticulocytes, pass through filter 12 and are collected in waste collection bag 16.

After all of the unwanted blood products 18 (e.g., non-nucleated cells) have passed through the filter, the nucleated cell population remaining on the filter contains the cells of interest, NRBC's, as a subpopulation. As shown in FIG. 2, valves 10 and 22 are closed. A syringe 36 containing elution solution 40 is attached to tubing 26. Valves 24 and 28 are opened. A syringe 36 containing elution solution 40 is attached to tubing 26. Valves 24 and 28 are opened. Elution fluid 40 is forced backward through the filter and causes the nucleated cells 7 to be released from the filter. An elution fluid such as one recommended by the manufacturer of the filter may be used. Alternatively, one aspect of the invention includes use of an elution fluid containing one or more of sodium or potassium fluoride (e.g., 0.01 to 100 mg/mL), pseudoephedrine (e.g., 0.1 to 100 mg/L), EDTA (e.g., 1 to 10 mM), ACD-A (e.g., 0.01 to 10%) trehalose (e.g., 0.01 to 10 gm/L), maltose (e.g., 0.01 to 10 gm/L), dextran (e.g., 0.01 to 3.0%, 100-500 MW), F-68 (e.g., 0.001 to 10 mg/mL), sodium or potassium sulfate (e.g., 1 to 100 mM), or sodium or potassium phosphate (e.g., 1 to 100 mM). In one embodiment, the elution solution includes about 25 ug maltose and about 75 ug trehalose in about 25 mL phosphate buffered solution (PBS). Elution fluid 40 and cells 7 are collected in collection bag 30 to yield an enriched fetal nucleated cell population 42. These released cells and the elution fluid are collected into vials.

Figure 3:
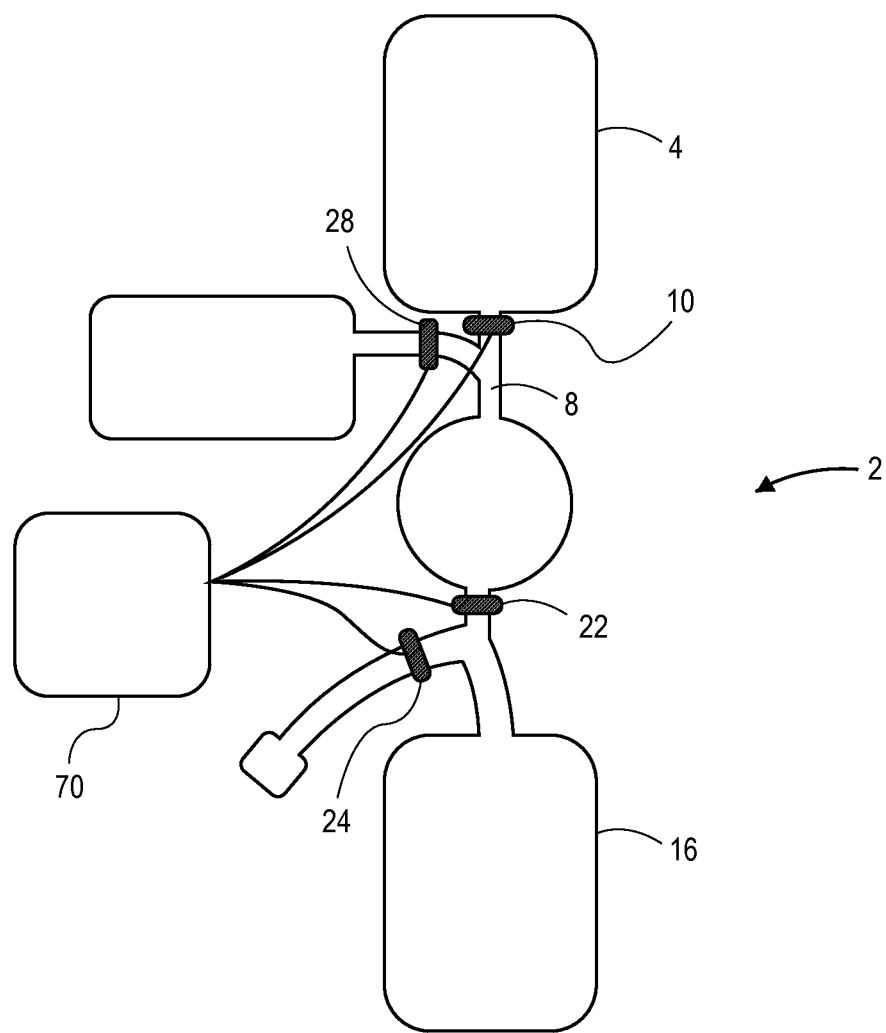
FIG. 3 shows a cell smear tool creating a layer of cells on a surface.

Machinery may be provided to automate the filtration and cell release process. The machinery may control either or both of the flow rate and amount of fluid that moves through the filter system. FIG. 3 shows controller 70 according to an embodiment of the invention configured to control flow rates of sample, waste, elution fluid, and/or elution fluid containing fetal nucleated cells through valves 10, 28, 22, and/or 24. A flow rate equal to 0.2-50 ml/second may be used. The volume of fluid that moves through the filter system may be from 5 mL to 500 mL. Controlling flow rates can have a significant impact on the cell population that is recovered: If the flow rate is too high, cells of interest may be driven deeply into the filter making them harder to recover. Also, if the flow rate is too high, cells may be damaged by hydrodynamic forces. If the flow rate is too low on the release backflush, cells of interest may not be recovered; they will remain trapped by the filter. Machinery for automation of filtration and cell release process may include a computer controlled valve and pump system whereby the fluid flow paths through the filtration device can be controlled by a series of valves and manifolds. One type of valve particularly well suited is the pinch tube valve since it can control fluid flow without coming in contact with the fluids. This is advantageous for avoiding cross-contamination between samples and making for a fully disposable filtration system where expensive components such as valves do not need to be discarded or cleaned. The flow through the filtration device can be accomplished by a combination of gravity and mechanical pump systems such that both rate of flow and flow velocity profiles can be set and controlled by computer hardware and software.

The machinery may also improve the repeatability of the process and reduce cycle time. For example, the automation may enable high speed processing while maintaining standardization of sample handling. Also, the filtration process requires control of valves, volumes, and flow rates during the process. The automation will minimize operator/technique dependent variability.

The next step may be concentration by centrifugation. The cells may be stained and counted (e.g., using the optical density of the suspension as a measure of cell count) before centrifugation. Alternatively, or additionally, cells may be stained after centrifugation. After the cells have been collected in a centrifuge tube (having, e.g., total volume of approximately 50 ml dilute cell suspension), the tube is spun in a centrifuge (e.g., for 15 minutes at 500×g at room temperature) to concentrate the cells into a pellet at the bottom of the tube. The resulting pellet volume is approximately 100 µl to 300 µl. It is possible to stain the cells before centrifugation as well as count the number of cells in the pre-centrifuge suspension.

Measuring the cell count in the pre-centrifuge suspension using the optical density of the suspension allows the automation of the removal of supernatant and the automation of the addition of stabilizers and stain (e.g., 0.01-10% ACD-A, 0.01 to 3% of 10 K-400 K MW dextran, 1-10 mM EDTA, 0.01 to 10 g/L maltose, 0.1 to 100 mg/mL pseudoephedrine, 0.01 to 10 g/L Trehalose, 0.01 to 100 mg/mL sodium or potassium fluoride, 1 to 100 mM sodium or potassium phosphate, and/or 1 to 100 mM sodium or potassium sulfate. In one embodiment, stabilization fluid may contain sodium sulfate (less than about 20 grams per L), sodium chloride (less than about 2 grams per L), imidazole (less than about 3 grams per L), sodium fluoride (about 2 grams per L), and pseudoephedrine (less than about 0.1 grams per L). In some cases, measuring the cell count after centrifugation may lead to large errors in cell counts because the volume is so small and the optical density is very high (opaque).

Automating the volume of stain and stabilizer that is added to the suspension prior to centrifugation allows the stain and stabilizer to reach and affect all cells in a more homogeneous manner. Adding stain and stabilizer after centrifugation in some cases may lead to non-homogeneous staining and stabilization because the cells have already started to clump and the large solid to liquid ratio in the pellet may inhibit the even distribution of the additives.

Adding a nuclear stain prior to the creation of the monolayer reduces the number of processing steps required to enable scanning. In some cases, staining after the monolayer has been created requires a fixation step that adds complexity, handling, and cost to the sample processing and may modify the cell morphology, reducing the effectiveness of the automated digital microscopy.

Automating the amount of supernatant that is removed after centrifugation may improve the repeatability of the final cell suspension that is used to create the monolayer. Standardizing the solid to liquid ratio of the monolayer suspension generates more uniform distribution of cells on each substrate and also improves the variability between individual smears on slides. Maximizing the cell distribution uniformity enables the extrapolation of one slide's results to all slides in a single patient set. This ability to accurately extrapolate results means that a smaller number of slides must be put through the imaging system and reduces the necessary cycle time per patient. In addition, tight control of the suspension density minimizes or eliminates the need for a trial and error approach to creating a monolayer with an appropriate cell density for automated digital microscopy.

Figure 4:
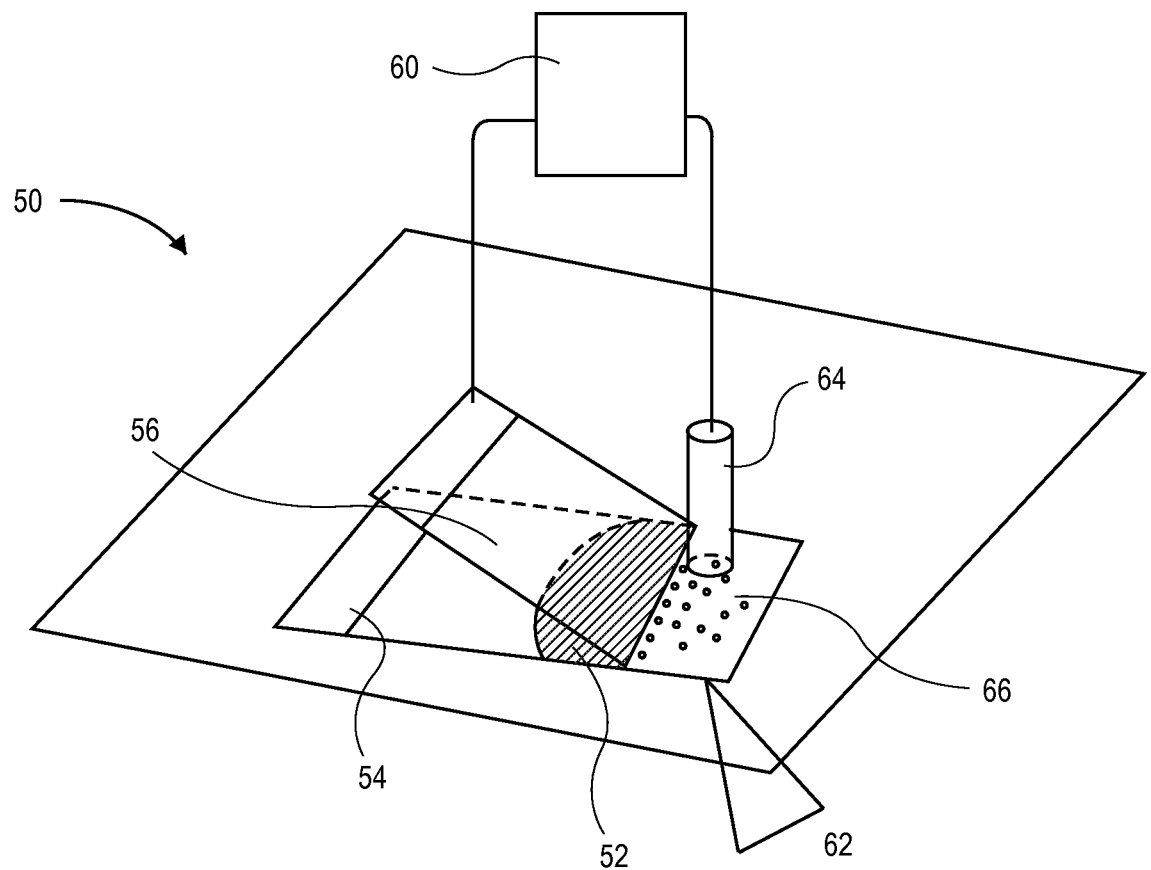
FIG. 4 shows a system for automating the process using a device such as the one shown in FIG. 1.

After concentration in the centrifuge, the cells are resuspended. Using the cell count as a guide for the final required liquid volume, all unwanted suspension fluid is removed from the centrifuge vial until only the desired total volume remains in the vial. The remaining supernatant and cells are then gently mixed (e.g., by agitation or by repeated aspiration and dispense cycles using a pipette). Automated removal of the supernatant based on the pre-centrifugation cell count enables the creation of a monolayer that is optimized for automated digital microscopy and rare cell identification. Next, a monolayer is created. The resuspended pellet is then dispensed onto a substrate, such as clear glass of standard microscope slide thickness. Using an automated smear tool, this droplet is spread evenly across the substrate surface in a manner that minimizes clustering and overlap of cells while maximizing the number of cells per unit area. FIG. 4 shows a cell smear tool 50 according to one embodiment of the invention. A sample of enriched fetal nucleated cells 52 is placed on surface 54. Cell smear blade 56 is moved by cell smear tool controller 60 across sample of enriched fetal nucleated cells 52 to create a layer of cells 66 on surface 54.

Prior automated smearing tools merely recreated the human motion that has historically been used to create blood smears by moving only with a single action linear speed motion in one axis (e.g., along the long Y axis of the slide). In one aspect of the invention, the automated smear tool moves in both X and Y while making essentially a monolayer smear. The motion patterns of a stage (e.g., an XY motorized stage) controlled by the computer software are unique. In some embodiments, the motion goes across the short X axis of the slide. The use of the short X axis motion can be helpful in creating a suspension along the smear slide before actual forward motion of the smear begins. In some embodiments, the software runs open loop (without monitoring cell density).

In other embodiments, cell density is monitored. In FIG. 4 light 62 illuminates layer of cells 66 and images are captured by detector 64 and used to determine cell density. In one embodiment, feedback from detector 64 is used to guide controller 60 to change parameters of cell smear blade 56 to control the density of cells 66 on surface 54. The smear density could be monitored, e.g., by using blue light (which will be absorbed by the hemoglobin) or red light (which will measure all cells). Higher attenuation of the light indicates a denser cell layer; lower attenuation indicates a less dense cell layer. In some embodiments, the system is configured to vary parameters such as angle of smear and/or speed of smear in real time to assure that the uniformity of the monolayer is maintained.

The automated smear tool varies its speed during the monolayer smearing process to control the density of cells that are applied per unit area to the substrate. The software speed may vary, for example, from 0.1 mm/sec to 500 mm/sec. The software may have a starting speed and ending speed for the smear tool which are the same, or they may differ from each other. In the case where the starting speed and ending speeds differ, the smear tool may change speed automatically in real time during the smear process. The rate of change may be linear or exponential. It could also vary sinusoidally or be varied using any other continuous function during the smear. The automated smear tool optimizes the initial droplet pickup and spread more or less normal to the main direction of smear. This may improve the overall uniformity of the smear normal to the main direction of smear.

The automated smear tool may move in a zigzag pattern during the smearing process to improve the homogeneity of the suspended cell population and the homogeneity of the cell population distributions per unit area. The automated smear tool can create smears in any size, such as 1"×2" or 5"×5" (125 mm×125 mm).

The smear tool may have any motion that aids in distributing the cells. The smear tool may move in both the X and Y directions during both the pickup of the initial cell droplet and during the actual smearing process itself. The motion(s) of the smear tool may be circular, zigzag, forward, backward, side to side with no forward or backward motion, diagonal, serpentine (move in +X, move in +Y, move in −X, move in +Y, repeat). These motions are useful for two reasons: they make the height of the meniscus even across the face of the smearing tool and improve the uniformity of the cell density in the direction normal to the main axis of the smear. Second, the starting and stopping motion helps to move cells up into suspension and improve the homogeneity of the cell populations distribution within the meniscus behind the smearing tool.

The automated smear tool may be controlled by a GUI that allows the user to set parameters such as smear speed, velocity profile, cross motion Y axis suspension parameters and motion distance. The parameters may be set up and stored based on an initial test smear.

The smear tool may have notched edges or polished edges, or it may be uncharged or have varying surface charge. The smear tools and/or smear slides may be made of glass or material other than glass.

Figure 5:
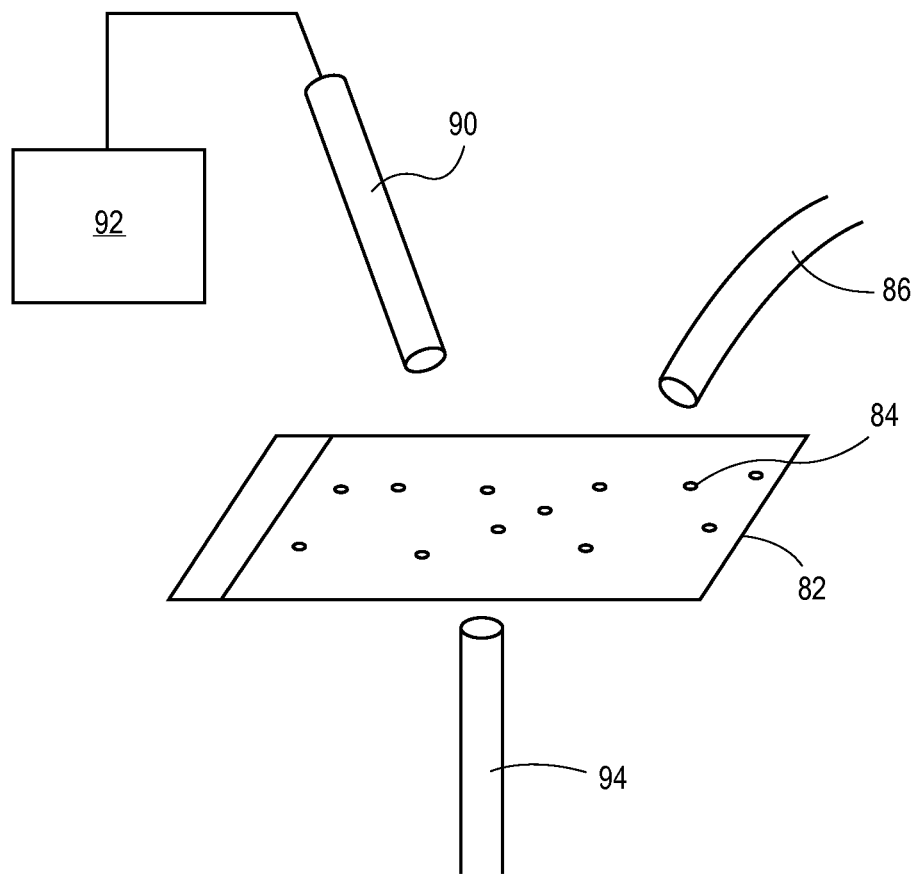
FIG. 5 shows an automated system used to identify fetal nucleated cells.

The monolayer is then imaged using an automated microscopy platform. In general any microscopy platform may be used with the requirement that the microscopy platform has the capability to provide transmitted illumination (e.g., 380 nm-800 nm range) and coaxial illumination (e.g., in the 350 nm-364 nm range to excite the nuclear stain). FIG. 5 shows an automated microscope system to identify fetal nucleated cells according to one aspect of the invention. Light 86 or light 94 is delivered to surface 82 containing fetal nucleated cells 84 and other cells. Light from the cells on surface 82 is detected through microscope 90. Microscope 90 is moved across surface 82 by controller 92.

A pair of images is acquired for each XY location on the substrate. For example, one image uses 420 nm illumination, and one image uses the fluorescent illumination. The XY locations are selected in such a way that the entire area of the substrate is imaged. For each location, the image pair is used to determine locations where the 420 nm light is absorbed which indicates the presence of hemoglobin. The fluorescent image is used to determine the location of nuclear material in the field of view. Where the characteristics of shape and brightness of the nucleus match the known characteristics of an NRBC and hemoglobin is also present, an NRBC candidate has been found and this candidate is added to a list of candidate cells.

Note that red light in the range of 620 nm or higher may also be used since this red light will not be absorbed by either nuclear material or by hemoglobin. The red image will thus only contain the actual physical structure of the cells: cell edges, texture or background artifacts from the suspension medium, and non-cell particles on the slide. This true structure information may be used when determining the amount of hemoglobin signal that is coincident with nucleus locations in order to reduce false positives. (It is not possible to separate signal generated by structural edges from signal generated due to 420 nm absorbance using the 420 nm/fluorescent image pair only.) The initial imaging may be done at a low magnification (e.g., 10×) to improve system speed and the highest scoring. NRBC candidates are revisited at higher magnification to verify the status as true NRBCs.

A high speed automated digital microscopy platform may be used to collect the images. Any set of image pairs (e.g., 420 nm/fluorescent) or triads (e.g., 420 nm, 630 nm, fluorescent) can be used to sort the cells into subpopulations of white cells, non-nucleated red cells, and nucleated red cells. The cell identification and subpopulation grouping algorithm does not interrogate cells that are known to be outside the population of interest.

The combination of the 420 nm and fluorescent imaging is made possible due to the sample preparation steps that preserve the morphology of the cells and maintain the hemoglobin intact through the creation of the monolayer. A unique algorithm can be used to determine the NRBC character of any cell. The heart of the algorithm is the ability to determine the coincidence of 420 nm absorption and nuclear fluorescence (completely dark NRBCs) in addition to the adjacency of 420 nm absorption to nuclear fluorescence. The steps of the algorithm may include:

Flatten the illumination (make the image brightness even across the complete image to correct for dimness in the image corners which may arise due to optical system aberration).

Apply the image flattening to both fluorescent and 420 nm transmission images.

Segment the images to determine which pixels belong to foreground (nuclei and hemoglobin) and which pixels belong in the background. Image segmentation removes noise from the images and may reduce the number of pixels that must be processed in the remaining steps.

Enumerate (count and number sequentially) the individual nuclei in the fluorescent image.

Calculate their complexity and average brightness (#edge pixels$^2$)/(# interior pixels) tends to $4\pi$ or 12.56 for perfectly round nuclei. NRBC nuclei tend to be round (low complexity) and bright.

For the subpopulation of the nuclei with the lowest complexity, determine the hemoglobin absorbance coincident to the nuclei and the hemoglobin absorbance around the perimeter of the nuclei. For example, the 50%, 25%, or 10% least complex are examined. (The higher nuclei do not need to be examined.)

Any parameters of the nuclei may be examined. In some embodiments, the brightness, complexity, and/or hemoglobin absorbance of the nuclei are measured. The cells that cluster in the 3-space region of high hemoglobin absorbance, low complexity, and high brightness have a high likelihood of being NRBCs and are graded as very likely candidates to be NRBCs.

In a similar manner the white cells may be binned into their subpopulations (e.g., segmented neutrophils have high complexity and large whites), and every WBC that is put into a specific bin removes another cell from the NRBC candidate pool.

Both hemoglobin absorbance and nuclear fluorescence signals may be calculated relative to the average brightness of the foreground and the average brightness of the background. In this manner it is possible to make comparisons intra-site. (One pair of 420 nm/fluorescent images can be compared to another pair of 420 nm/fluorescent images.) If relative measures are not used then variations larger than a single field of view will impact the ability to correctly detect the cells of interest across the entire slide. Examples of large scale variations include: variations in fluorescent staining, variations in RBC hemoglobin lysing, and illumination changes (lamp warming up or failing).

The storage of the NRBC candidate XY locations enables the use of less FISH reagent which reduces cost. The FISH reagents may be applied only to the sites where NRBCs have been located. After FISH is complete, these XY locations are used again to revisit the NRBCs and interrogate the final genetic testing result.

The XY locations of the candidate NRBCs may also be used to control a microdissection system. Microdissection may be used to pick up the NRBCs and physically segregate them away from the non-NRBC cell population. This microdissection enrichment process may be used to provide high purity DNA samples for use in microarray applications, PCR, or other DNA analysis methods.

The image can then be analyzed. The use of the 420 nm and fluorescent image pairs (or a 420 nm, 630 nm, and fluorescent image trio) to find NRBC candidates depends on the following characteristics of NRBCs:
 (1) NRBCs are associated with hemoglobin absorbance (dark pixels in the 420 nm image). Sometimes the hemoglobin absorbance area covers the same set of pixels as the nuclear fluorescence. In other cases the hemoglobin absorbance is adjacent to the fluorescent signature of the nuclear material.
 (2) NRBC nuclei tend to be single nuclei and tend to be round (low complexity)
 (3) NRBC nuclei tend to have a brighter fluorescent signal that other cell nuclei in the same image
 (4) NRBC nuclei tend to be smaller than most other nuclei because they are in the process of condensing and being forced out of the cell (e.g., by apoptosis)

Next is the fixation step. The cells are treated with a non-crosslinking fixation in preparation for FISH. This fixation is performed in the presence of stabilizers which improve the FISH results, maintain RBC morphology and hemoglobin signal for later relocation/revisit of the fetal NRBCs using the previously stored XY locations. Fixation may include EtOH (40 to 90%), glyoxal (0.1 to 25%), methanol (0.1 to 10%) and or isopropanol (0.1 to 10%) for (15 sec to 10 min) preceded by a −20 degree centigrade methanol dip for 30 seconds to 2 days.

Stabilizers may include Sodium or potassium fluoride (0.01 to 100 mg/mL), pseudoephedrine (0.1 TO 100.0 mg/L), EDTA (1 to 10 mM), ACD-A (0.01 to 10.0%) trehalose (0.01 to 10 gm/L), maltose (0.01 to 10.0 gm/L, dextran (0.01 to 3.0%, 100-500 MW), F-68 (0.001 to 10 mg/mL), sodium or potassium sulfate (1 to 100 mM), sodium or potassium phosphate (1 to 100 mM).

One suitable fixation process includes the following steps: Freeze substitution prefix in −20° C. MeOH for 10 minutes; and postfix treatment in EtOH, glyoxal, MeOH, and isopropanol. This process is beneficial in that it avoids the use of formaldehyde and glutaraldehyde. Waste disposal issues are eliminated, and DNA and RNA retrieval is made easier because no cross linking occurs.

Genetic testing and fetal/maternal differentiation can now be performed. Standard FISH may be performed on the NRBCs that are found using the automated cell identification algorithms. In addition, human TSIX sequences may be used to definitively identify the cells as fetal female and not maternal. TSIX expression stops on both human X chromosome between 2 and 4 years of age. Adult females do not express the TSIX gene. Thus, including a probe for TSIX in the FISH process will allow a definitive determination of fetal female versus maternal status for all candidate NRBCs being interrogated. A FISH signal at the TSIX region of the nucleus will only be present if the cell is fetal. The presence of a Y chromosome determines if the nucleated red blood cell is from a male fetus.

It is also important to note that nuclei of the NRBCs are in the process of apoptosis and are being condensed in preparation for ejection from the cell. Highly condensed nuclei tend to have a lower efficiency from FISH treatment than do non-condensed nuclei. Two novel approaches to improving the FISH efficiency for condensed nuclei are:
 (1) Perform FISH in a vacuum or under lower than atmospheric pressure; or
 (2) Physically crush the cells and the nuclei prior to the application of the FISH probes by revisiting the XY locations of candidates and pressing on them in a controlled manner. The cells to be crushed or flattened would be the NRBCs identified by the DAPI/420 nm scan. On the same microscope platform that did the DAPI/420 nm scan a motorized nosepiece could rotate over the "crushing head". This could be, for example, a spring loaded small diameter flat ended steel rod, and automatically lowered onto the slide at the location of the NRBC to be crushed. The crushing force applied may be controlled by the spring force constant in the crushing rod. The rod diameter may be small, for example, 100 microns in diameter so it would crush the target NRBC and the perimeter of cells around it. An absolute XY location accuracy may not be required. The small diameter also allows for very high crushing forces to be applied to the localized area.

The TSIX expression and the variation of TSIX expression versus human age is described in *Species Differences in TSIX/Tsix Reveal the Roles of These Genes in X-Chromosome Inactivation*; Migeon, Barbara R.; Lee, Catherine H.;

Chowdhury, Ashis K.; Carpenter, Heather; doi:10.1086/341605 (volume 71 issue 2 pp. 286-293).

Crushing cells to improve access to the nuclear material is described in *Cell Crushing: A Technique for Greatly Reducing Errors in Microspectrometry*; Davies, H. G; Wilkins, M. H. F; Boddy, R. G. H. B.; Experimental Cell Research 6/(550-553); 1954.

Novel aspects of the invention include: The combination of TSIX with FISH for the definitive determination of fetal female/maternal status of cells; the use of vacuum to improve FISH results in fetal genetic testing; and the use of physical crushing of cells to improve access to the nuclear material.

Stored XY locations may be used to record genetic test results. The XY locations of the candidate NRBCs are used throughout the processing of the cells for genetic testing. It is possible to apply FISH probe to only those cells of interest, thus reducing the overall cost per test per patient. It is also possible to revisit the cells and physically remove them from the substrate for physical segregation away from the population of non-NRBCs, thus increasing the percentage of fetal DNA relative to maternal DNA.

It is possible to revisit the XY locations of the NRBC candidates to interrogate the FISH results and fetal/maternal determination. It is also possible to revisit the XY locations of the NRBC candidates and physically decondense the nuclei.

The cells prepared by the methods described herein may be subject to antibody analysis. For example, several specific erythrocytic hemoglobin antibodies are available for the differential identification of fetal RBC's that occur in maternal peripheral blood (Zheng et al. 1999 *Fetal cell identifiers: results of microscope slide-based immunocytochemical studies as a function of gestational age and abnormality*. Am. J. Obstet. Gynecol. 180:1234-1239). Standard antibody staining techniques for fetal and embryonic hemoglobins may be performed on the NRBC's that are found in maternal blood by filtering samples, preparing monolayers on slides and locating NRBC's with the automated cell identification algorithm software. Adults do not express the embryonic hemoglobin, epsilon, while fetal RBC's may contain this embryonic hemoglobin up until the end of the first trimester (Mevron et al. 1999. *Improved specificity of RBC detection in chorionic villus sample supernatant fluids using anti-zeta and anti-epsilon monoclonal antibodies*. Feta. Diagn. Ther. 14:291-295). Antibodies against other embryonic (zeta) and fetal hemoglobins may be used with anti-epsilon to increase the specificity of identification of fetal NRBC's, but these antibodies will also recognize zeta and fetal hemoglobin expression in adult sickle cell anemics and thallesemics. Fetal hemoglobin is expressed during the last two trimesters of pregnancy and shifts to beta-hemoglobin after birth.

EXAMPLE

FIG. 6 shows data obtained from maternal blood samples after enrichment for fetal nucleated cells according to one embodiment of the disclosure. The maternal blood samples were passed over leukocyte depletion filters and cells remaining on the filter were eluted using elution buffer as described above. The cells were smeared onto slides and stained with DAPI to detect nucleated cells and subject to immunohistochemistry using anti epsilon hemoglobin antibody to detect the presence of fetal cells. A portion (% of sample analyzed) of the slides were illuminated with 420 nm and UV light to distinguish nucleated from non-nucleated cells, and cells with hemoglobin from cells without hemoglobin. Cells were classified as non-nucleated red blood cells (RBC), white blood cells (WBC), and candidate nucleated red blood cells and the ratio of red blood cells to white blood cells (RBC:WBC) in the sample calculated. A % packing density was calculated based on the total number of cells counted. Fetal nucleated Red Blood Cells in the fields analyzed was confirmed using anti epsilon hemoglobin antibody (#fnRBCs identified), and the predicted number of fetal nucleated red blood cells (#fnRBCs extrapolated) in each sample extrapolated.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of identifying a nucleated fetal cell, the method comprising the steps of:
   obtaining a maternal blood sample;
   removing non-nucleated cells from the maternal blood sample to thereby create an enriched maternal blood sample;
   adhering cells from the enriched maternal blood sample to a surface;
   staining the cells with a nuclear stain to thereby produce a plurality of cells having stained nuclei;
   generating a pair of images corresponding to the same cell wherein one image of the pair of images shows the stained nucleus of the cell;
   applying an algorithm to the pair of images to determine that the shown cell is a nucleated red blood cell;
   treating the nucleated red blood cell with a fetal identifier after the applying an algorithm step to thereby generate a treated cell; and
   performing an analysis on the treated cell using the fetal identifier to identify the treated cell as a nucleated fetal cell.

2. The method of claim 1 wherein the analysis is selected from the group consisting of in situ hybridization and immunohistochemistry, the method further comprising scanning the surface with an automated microscope after the adhering step.

3. The method of claim 2 wherein performing comprises treating with an antibody selected from the group consisting of anti-zeta hemoglobin and anti-epsilon hemoglobin if the analysis is immunohistochemistry.

4. The method of claim 1 wherein generating a pair of images comprises generating a first image with transmitted illumination and a second image with coaxial illumination.

5. The method of claim 4 wherein generating a first image with transmitted illumination comprises generating a first image with transmitted illumination with a wavelength between about 380 nm and 800 nm.

6. The method of claim 4 wherein generating a first image with transmitted illumination and a second image with coaxial illumination comprises generating the second image with coaxial illumination with a wavelength between 350 nm and 364 nm.

7. The method of claim 1 further comprising selectively placing fetal identifiers on a plurality of candidate fetal cells.

8. The method of claim 1 wherein applying an algorithm comprises the steps of:
flattening at least one image;
segmenting at least one image and thereby defining foreground and background pixels;
removing background pixels from at least one image to generate a transformed image;
enumerating nuclei in the transformed image to generate enumerated nuclei; and
calculating at least one of complexity and brightness for at least one enumerated nuclei, wherein low complexity or high brightness indicates a fetal cell character.

9. The method of claim 1 wherein applying an algorithm comprises calculating a brightness of a background of the surface and a brightness of a foreground of the surface, and comparing a measurement of the pair of images to one or both of the background brightness and the foreground brightness.

10. The method of claim 1 further comprising fixing the sample with a non-crosslinking fixative before the performing an analysis step.

11. The method of claim 1 further comprising physically segregating an identified nucleated fetal cell from other cells adhered to the surface.

12. The method of claim 11, wherein physically segregating comprises microdissecting the nucleated fetal cell.

13. The method of claim 11, wherein physically segregating comprises picking up the nucleated fetal cell from surface.

14. The method of claim 1 wherein performing an analysis comprises using an anti-embryonic hemoglobin antibody to thereby identify the treated cell as a nucleated fetal cell.

15. The method of claim 1, wherein staining the cells comprises treating the cells with 4',6-diamidino-2-phenylindole (DAPI).

16. A method of identifying a nucleated fetal cell, the method comprising the steps of:
obtaining a maternal blood sample;
removing non-nucleated cells from the maternal blood sample to thereby create an enriched maternal blood sample;
creating a monolayer of cells from the enriched maternal blood sample on a surface;
staining the nuclei of the cells in the monolayer with a nuclear stain;
transmitting a hemoglobin absorbable light through the monolayer;
generating a pair of images showing a cell in a portion of the monolayer, wherein the first image shows the stained nucleus of said cell and a second image shows the absorbance of the hemoglobin absorbable light through said portion;
applying an algorithm to the pair of images to categorize said cell as a white cell, a non-nucleated red cell, or a nucleated red cell;
performing an analysis using a fetal identifier on said cell if the cell is categorized as a nucleated red blood cell by the algorithm; and
identifying said cell as a nucleated fetal red cell after the fetal identifier indicates the presence of fetal cellular material in said cell.

17. The method of claim 16 wherein generating a pair of images comprises generating a first image with transmitted illumination and a second image with coaxial illumination.

18. The method of claim 17, wherein generating a first image with transmitted illumination comprises generating a first image with transmitted illumination with a wavelength between about 380 nm and 800 nm.

19. The method of claim 17, wherein generating a first image with transmitted illumination comprises generating a first image with transmitted illumination with a wavelength around 420 nm.

20. The method of claim 16, wherein performing an analysis comprises selectively placing fetal identifiers on a plurality of portions of the surface, wherein each portion contains a candidate fetal cell.

21. The method of claim 16, wherein applying an algorithm comprises calculating a brightness of a background of the surface and a brightness of a foreground of the surface, and comparing a measurement of the pair of images to one or both of the background brightness and the foreground brightness.

22. The method of claim 16 further comprising storing a location of the pair of images.

23. The method of claim 22 further comprising locating a nucleated cell based on the stored location.

24. The method of claim 16, wherein the performing step comprises treating with a stabilizer.

25. The method of claim 16, wherein the applying an algorithm step comprises categorizing said cell as a nucleated red cell after the second image shows the absorbance of hemoglobin absorbable light coincident with the location of the stained nucleus shown in the first image.

26. The method of claim 16 further comprising physically segregating a cell categorized by the algorithm as a nucleated red blood cell from other cells in the monolayer.

27. The method of claim 26, wherein physically segregating comprises microdissecting the cell.

28. The method of claim 26, wherein physically segregating comprises picking up said cell from the monolayer.

29. The method of claim 16, wherein staining the nuclei comprises treating the cells with 4',6-diamidino-2-phenylindole (DAPI).

30. The method of claim 16 further comprising adjusting density of cells in the maternal blood sample before the creating a monolayer step.

* * * * *